United States Patent
Darbandi et al.

(10) Patent No.: US 10,835,418 B1
(45) Date of Patent: Nov. 17, 2020

(54) MEIBOMIAN GLAND THERMAL TREATMENT APPARATUS

(71) Applicants: Sarah S. Darbandi, Jacksonville Beach, FL (US); Bejan M. Darbandi, Chanhassen, MN (US)

(72) Inventors: Sarah S. Darbandi, Jacksonville Beach, FL (US); Bejan M. Darbandi, Chanhassen, MN (US)

( * ) Notice: Subject to any disclaimer, the term of this patent is extended or adjusted under 35 U.S.C. 154(b) by 397 days.

(21) Appl. No.: 15/696,735

(22) Filed: Sep. 6, 2017

Related U.S. Application Data

(60) Provisional application No. 62/383,980, filed on Sep. 6, 2016.

(51) Int. Cl.
- *A61F 9/007* (2006.01)
- *A61N 1/40* (2006.01)
- *A61B 18/12* (2006.01)
- *A61F 7/00* (2006.01)

(52) U.S. Cl.
CPC .......... *A61F 9/00772* (2013.01); *A61N 1/403* (2013.01); *A61B 18/12* (2013.01); *A61F 2007/0004* (2013.01)

(58) Field of Classification Search
CPC combination set(s) only.
See application file for complete search history.

(56) References Cited

U.S. PATENT DOCUMENTS

| | | | |
|---|---|---|---|
| 2,545,724 A * | 3/1951 | Curtis | A61F 7/007 607/109 |
| 3,333,586 A | 8/1967 | Bellis et al. | |
| 3,667,476 A | 6/1972 | Muller | |
| 4,261,364 A | 4/1981 | Haddad et al. | |
| 4,554,911 A * | 11/1985 | Nielsen | A61H 15/0092 132/333 |
| 4,763,657 A * | 8/1988 | Chen | A61N 1/36021 128/907 |
| 4,778,457 A | 10/1988 | York | |
| 5,133,702 A * | 7/1992 | Py | A61F 9/0008 604/298 |
| 5,158,082 A | 10/1992 | Jones | |
| D331,288 S | 11/1992 | Yuen | |
| D347,283 S | 5/1994 | Von Winckler | |
| 5,314,456 A | 5/1994 | Cohen | |

(Continued)

*Primary Examiner* — Kaitlyn E Smith
(74) *Attorney, Agent, or Firm* — Albert W. Watkins

(57) ABSTRACT

A portable handheld meibomian gland thermal treatment apparatus includes a housing holding a battery and necessary electrical components. A generally rectangular and concave thermal applicator tip terminates the housing, and applies precisely controlled heat to a single eyelid. A bend in the housing enables the apparatus to be held in position with the apparatus extending from the eyelid generally parallel to the ground and then from the bend sloping away from the viewing plane, either down toward the ground or upward away from the ground. As a result, a person may still keep one of the two eyelids on the treatment eye open and see past the housing and supporting hand, thereby simultaneously performing treatment while also performing other tasks. Various embodiments illustrate automatic on and off operation; a telescoping applicator having long-travel application force regulation; and a method of thermally treating meibomian gland dysfunction using the apparatus.

14 Claims, 5 Drawing Sheets

(56) References Cited

U.S. PATENT DOCUMENTS

| | | | |
|---|---|---|---|
| 5,551,949 A * | 9/1996 | Kim | A61H 23/02 601/15 |
| 5,643,336 A | 7/1997 | Lopez-Claros | |
| 5,690,608 A * | 11/1997 | Watanabe | A61H 15/0092 601/19 |
| 5,720,773 A | 2/1998 | Lopez-Claros | |
| 6,001,070 A * | 12/1999 | Gebhard | A61F 7/007 601/15 |
| 6,052,904 A * | 4/2000 | Wetzel | B26B 19/044 30/346.51 |
| 6,155,995 A | 12/2000 | Lin | |
| 6,908,195 B2 | 6/2005 | Fuller | |
| 7,069,084 B2 | 6/2006 | Yee | |
| 7,211,070 B2 | 5/2007 | Soroudi | |
| 7,231,922 B2 | 6/2007 | Davison et al. | |
| 7,384,405 B2 * | 6/2008 | Rhoades | A46B 13/023 601/15 |
| 7,513,893 B2 | 4/2009 | Soroudi | |
| 7,544,204 B2 * | 6/2009 | Krespi | A61N 5/0603 128/898 |
| 7,833,205 B2 | 11/2010 | Grenon et al. | |
| D636,088 S | 4/2011 | Loew et al. | |
| 7,976,573 B2 | 7/2011 | Korb et al. | |
| 7,981,095 B2 | 7/2011 | Grenon et al. | |
| 7,981,145 B2 | 7/2011 | Korb et al. | |
| 7,981,146 B2 | 7/2011 | Korb et al. | |
| 7,981,147 B2 | 7/2011 | Korb et al. | |
| 8,007,524 B2 | 8/2011 | Korb et al. | |
| D645,565 S | 9/2011 | Smith et al. | |
| 8,025,689 B2 | 9/2011 | Korb et al. | |
| 8,083,787 B2 | 12/2011 | Korb et al. | |
| 8,128,673 B2 | 3/2012 | Korb et al. | |
| 8,128,674 B2 | 3/2012 | Korb et al. | |
| 8,137,390 B2 | 3/2012 | Korb et al. | |
| 8,187,310 B2 | 5/2012 | Korb et al. | |
| 8,187,311 B2 * | 5/2012 | Korb | A61F 9/00772 607/88 |
| 8,267,907 B2 | 9/2012 | Soroudi | |
| 8,491,508 B2 * | 7/2013 | Smith | A61F 7/007 601/18 |
| 8,506,539 B2 | 8/2013 | Guillon et al. | |
| 8,523,928 B2 | 9/2013 | Korb et al. | |
| 8,617,229 B2 | 12/2013 | Korb et al. | |
| 8,628,504 B2 | 1/2014 | Grenon et al. | |
| 8,632,578 B2 | 1/2014 | Korb et al. | |
| 8,685,073 B2 | 4/2014 | Korb et al. | |
| 9,067,060 B2 * | 6/2015 | Neev | A61N 5/0613 |
| 9,782,574 B2 * | 10/2017 | Simmers | A61M 37/0015 |
| 2007/0016256 A1 | 1/2007 | Korb et al. | |
| 2007/0016271 A1 * | 1/2007 | Hammond | A61F 7/007 607/96 |
| 2007/0191821 A1 * | 8/2007 | Boxer Wachler | A61B 18/20 606/9 |
| 2008/0109052 A1 * | 5/2008 | Grenon | A61F 9/00772 607/104 |
| 2008/0109053 A1 | 5/2008 | Grenon et al. | |
| 2009/0043365 A1 * | 2/2009 | Friedland | A61H 1/008 607/108 |
| 2009/0264971 A1 * | 10/2009 | Wickstead | A61F 7/03 607/108 |
| 2010/0076526 A1 * | 3/2010 | Krespi | A61N 5/0603 607/88 |
| 2010/0179623 A1 * | 7/2010 | Hofer | A61F 7/007 607/96 |
| 2012/0065556 A1 * | 3/2012 | Smith | A61F 7/007 601/89 |
| 2012/0209154 A1 * | 8/2012 | Williams, III | A61F 7/02 601/19 |
| 2012/0226268 A1 * | 9/2012 | Liu | A61N 5/0613 606/9 |
| 2012/0232538 A1 * | 9/2012 | Liu | A61N 5/0613 606/9 |
| 2014/0243607 A1 * | 8/2014 | Eckhouse | A45D 26/00 600/249 |
| 2015/0005750 A1 * | 1/2015 | Kelleher | A61F 9/00718 606/3 |
| 2015/0038926 A1 * | 2/2015 | Park | A61F 7/007 604/310 |
| 2015/0057701 A1 * | 2/2015 | Kelleher | A61H 23/0263 606/204.15 |
| 2015/0121900 A1 * | 5/2015 | Yamazaki | A45D 34/04 62/3.3 |
| 2015/0216722 A1 * | 8/2015 | Choate | A61F 9/00772 606/162 |
| 2015/0320590 A1 * | 11/2015 | Whitehurst | A61F 7/007 607/109 |
| 2015/0327653 A1 * | 11/2015 | Decaux | A45D 34/041 604/20 |
| 2015/0360014 A1 * | 12/2015 | Decaux | A61M 35/003 604/20 |
| 2016/0030233 A1 * | 2/2016 | Millar | A61F 7/007 607/109 |
| 2016/0113836 A1 * | 4/2016 | Frazier | A61H 15/0092 601/20 |
| 2016/0242956 A1 * | 8/2016 | Pilby Gomez | A61F 7/007 |
| 2016/0256701 A1 * | 9/2016 | Furnish | A61B 18/14 |
| 2016/0317379 A1 * | 11/2016 | Mosaddegh | A61H 15/02 |
| 2016/0324719 A1 * | 11/2016 | Badmus | A61F 7/0241 |
| 2017/0128319 A1 * | 5/2017 | Decaux | A61H 23/0245 |
| 2017/0135852 A1 * | 5/2017 | Cheng | A61F 7/007 |
| 2017/0273823 A1 * | 9/2017 | Novkov | A61F 7/007 |
| 2018/0001108 A1 * | 1/2018 | Kelleher | A61N 5/0617 |
| 2018/0092773 A1 * | 4/2018 | Kelleher | A61F 9/00718 |
| 2018/0200106 A1 * | 7/2018 | Zoumalan | A61F 9/0008 |
| 2018/0235807 A1 * | 8/2018 | Nielsen | A61F 9/0008 |
| 2019/0060115 A1 * | 2/2019 | Novkov | A61H 1/00 |
| 2019/0254866 A1 * | 8/2019 | Whiteley | A61F 7/12 |
| 2019/0350750 A1 * | 11/2019 | Whitehurst | A61F 7/08 |

\* cited by examiner

MEIBOMIAN GLAND THERMAL TREATMENT APPARATUS

CROSS REFERENCE TO RELATED APPLICATIONS

The present application claims the benefit of U.S. provisional patent application 62/383,980 filed Sep. 6, 2016 of like title, the teachings and entire contents which are incorporated herein by reference.

BACKGROUND OF THE INVENTION

1. Field of the Invention

The present invention pertains generally to a hand manipulated ophthalmic tool, and more specifically to a thermal treatment apparatus having an internal battery and a heating element that is configured to apply heat to the eyelid in order to treat the meibomian glands.

2. Description of the Related Art

Dry eye syndrome is a common condition that has been estimated to afflict more than one in twenty persons, and as people age, the afflicted portion increases to more than half. In many cases of dry eye syndrome, a major contributor to the condition is evaporative dry eye caused by the meibomian (oil producing) glands of the upper and lower eyelids not functioning as they should. When we blink, this forces out liquid oil from the glands that forms a thin film over the top of a tear film coating the eye. This layer of oil serves as a barrier that substantially reduces evaporation, and also tends to keep the tear film in place. Unfortunately, because of multiple factors such as decreased blink from technology use, age, medications, environment, allergies, inflammation, and other factors, the oil may change from a liquid oil to a thick paste. In severe cases, the condition can progress to damaging scarring of the glands and even to permanent loss of the meibomian glands. With decreased gland function, patients suffer from worsening dry eye which can result in corneal scarring, infection, and in some cases the need for corneal surgery.

Many treatments for dry eye syndrome have been proposed over the years. Among these are the use of artificial tears to replace lost tear film, application of antimicrobial or steroid compounds, glasses and goggles to reduce tear evaporation, lacrimal plugs to reduce tear drainage, application of radiant energy such as RF and IR radiation, and various warm compresses and gel masks to improve the function of the meibomian glands.

An exemplary U.S. patent that illustrates the application of antimicrobial or steroid compounds, the teachings which are incorporated herein by reference, is U.S. Pat. No. 4,778,457 by York, entitled "Disposable applicator". Exemplary U.S. patents that illustrate glasses and goggles to reduce tear evaporation, sometimes with the additional application of heat or therapeutic chemicals, the teachings which are incorporated herein by reference, include: U.S. Pat. No. 6,155,995 by Lin, entitled "Structure of a multifunctional eye mask"; U.S. Pat. No. 6,908,195 by Fuller, entitled "Therapeutic eye and eye lid cover"; and U.S. Pat. No. 7,231,922 by Davison et al, entitled "Apparatus, system and method for treating dry eye conditions and promoting healthy eyes".

The warm compresses recommended for years by eye doctors are typically microwaveable gel masks that apply heat to both lids with the eyes closed. In addition to both eyes, these masks also undesirably apply heat to a portion of the face. Most patients have difficulty with compliance since this treatment requires either ten minutes with both eyes closed, or twenty minutes total with one eye closed by applying the heat for ten minutes to one eye followed by ten minutes to the other eye. Furthermore, the temperature of the masks can vary during through the treatment period, though this variance may be less extreme than that of the warm compresses such as wash cloths and the like. In addition, and whether a warm compress or gel mask, these warming treatment techniques suffer from the further disadvantage of requiring the patient to be tied to a household outlet, hot water faucet, or separate heat source such as a microwave oven.

Exemplary U.S. patents that illustrate warm compresses and gel masks improved over the basic warm wash cloth, the teachings which are incorporated herein by reference, include: U.S. Pat. No. 4,261,364 by Haddad et al, entitled "Electric warm compress for ophthalmic treatment"; U.S. Pat. No. 5,643,336 by Lopez-Claros, entitled "Heating and cooling pad"; U.S. Pat. No. 5,720,773 by Lopez-Claros, entitled "Method for treating biopsychiatric disorders"; U.S. Pat. No. 7,211,070 by Soroudi, entitled "Device and method for exothermic treatment of eyelid diseases"; U.S. Pat. No. 7,513,893 by Soroudi, entitled "Device and method for treatment of eyelid diseases"; U.S. Pat. No. 8,267,907 by Soroudi, entitled "Device and method for exothermic treatment of eyelid diseases"; and U.S. Pat. No. 8,506,539 by Guillon et al, entitled "Eyelid margin wipes comprising chemical means for temperature adjustment".

While radiant energy treatments such as RF and IR have been touted as overcoming some of the limitations of masks and compresses, these radiant energy sources can actually be harmful to the eyes.

Exemplary U.S. patents that illustrate various body applicator thermal devices and control circuits, the teachings which are incorporated herein by reference, include: U.S. Pat. No. 3,667,476 by Muller, entitled "Apparatus for monitoring body temperature and controlling a heating device to maintain a selected temperature"; U.S. Pat. No. 5,158,082 by Jones, entitled "Apparatus for heating tissue with a photoplethysmograph sensor"; U.S. Pat. No. 5,314,456 by Cohen, entitled "Therapeutic pad for relief of headache-related head, temple, neck and back pain"; U.S. Pat. No. 6,001,070 by Gebhard, entitled "Facial iron"; U.S. Pat. No. 7,384,405 by Rhoades, entitled "Oxygenating cosmetic instrument having various numbers of heads"; Des 331,288 by Yuen, entitled "Infra-red heat pain reliever"; Des 347,283 by Von Winckler, entitled "Rechargeable ifraderm"; and Des 636,088 by Loew et al, entitled "Hand-held applicator for applying energy to a body tissue region".

An early hand-held applicator having an eye piece taking the contour of an eyelid and providing heating or cooling thereto is illustrated in U.S. Pat. No. 2,545,724 by Curtis, entitled "Applicator for heat manipulation of the eyes", the teachings which are incorporated herein by reference. While the Curtis apparatus may be useful for the treating of an eyelid, the apparatus is not contoured to permit easy grasping and holding in a stationary position. Further, there is no moderation or control over the application force, meaning that a person of great training and skill must be employed to provide the treatment.

Several additional artisans have provided improvement in the treatment of Meibomian gland disorders over the techniques presented herein above. A number of these patents are assigned to TearScience, Inc. of Morrisville, N.C. The most relevant of these U.S. and published applications to the present invention, the teachings which are incorporated herein by reference, include: 2008/0109053 by Grenon et al, entitled "Melting meibomian gland obstructions"; U.S. Pat. No. 8,632,578 by Korb et al, entitled "System for providing heat treatment and heat loss reduction for treating meibomian gland dysfunction"; U.S. Pat. No. 8,685,073 by Korb et al, entitled "Apparatus for treating meibomian gland dysfunction"; and 2007/0016256 by Korb et al, entitled "Method and apparatus for treating gland dysfunction".

Other exemplary U.S. patents and published applications assigned to TearScience, Inc. of somewhat less relevance, the teachings which are nevertheless incorporated herein by reference, include: U.S. Pat. No. 7,833,205 by Grenon et al, entitled "Methods for treating meibomian gland dysfunction employing fluid jet"; U.S. Pat. No. 7,976,573 by Korb et al, entitled "Inner eyelid heat and pressure treatment for treating meibomian gland dysfunction"; U.S. Pat. No. 7,981,095 by Grenon et al, entitled "Methods for treating meibomian gland dysfunction employing fluid jet"; U.S. Pat. No. 7,981,145 by Korb et al, entitled "Treatment of meibomian glands"; U.S. Pat. No. 7,981,146 by Korb et al, entitled "Inner eyelid treatment for treating meibomian gland dysfunction"; U.S. Pat. No. 7,981,147 by Korb et al, entitled "Outer eyelid heat and pressure treatment for treating meibomian gland dysfunction"; U.S. Pat. No. 8,007,524 by Korb et al, entitled "Heat treatment and heat loss reduction for treating meibomian gland dysfunction"; U.S. Pat. No. 8,025,689 by Korb et al, entitled "Method and apparatus for treating meibomian gland dysfunction"; U.S. Pat. No. 8,083,787 by Korb et al, entitled "Method and apparatus for treating meibomian gland dysfunction"; U.S. Pat. No. 8,128,673 by Korb et al, entitled "System for inner eyelid heat and pressure treatment for treating meibomian gland dysfunction"; U.S. Pat. No. 8,128,674 by Korb et al, entitled "System for outer eyelid heat and pressure treatment for treating meibomian gland dysfunction"; U.S. Pat. No. 8,137,390 by Korb et al, entitled "System for providing heat treatment and heat loss reduction for treating meibomian gland dysfunction"; U.S. Pat. No. 8,187,310 by Korb et al, entitled "Method and apparatus for treating gland dysfunction"; U.S. Pat. No. 8,187,311 by Korb et al, entitled "Method and apparatus for treating gland dysfunction"; U.S. Pat. No. 8,523,928 by Korb et al, entitled "System for inner eyelid heat and pressure treatment for treating meibomian gland dysfunction"; U.S. Pat. No. 8,617,229 by Korb et al, entitled "System for outer eyelid heat and pressure treatment for treating meibomian gland dysfunction"; and U.S. Pat. No. 8,628,504 by Grenon et al, entitled "Method and apparatus for treating meibomian gland dysfunction employing fluid jet".

These TearScience, Inc. patents provide equipment that offers much advantage over prior art techniques. However, this equipment is complex and expensive, and so generally only suited to use by a treating physician in a larger care facility. As a result, and much like the Curtis patent incorporated herein above, this provides little benefit to a patient outside of the treatment facility.

Recognizing this continued deficiency in the prior art, several exemplary U.S. patents illustrate a device better suited for home use. These patents by particularly skilled artisans, the teachings which are incorporated herein by reference, include: U.S. Pat. No. 8,491,508 by Smith et al, entitled "Device and method for stimulating the meibomian glands of the eyelid"; and Des 645,565 by Smith et al, entitled "Device for stimulating the meibomian glands of the eyelid". Smith et al disclose a handheld device resembling an electric toothbrush that incorporates a temperature controlled oscillating head designed to apply both heat and massaging action to an eyelid. In spite of the many advances that are incorporated into the design of this Smith et al device, the device still lacks several features that are important or critical for good patient compliance. Among these are the ability to precisely control application pressure, the ability to ensure even contact and heating across the eyelid, and the explicit ability to use the device for treatment while keeping both eyes open.

An additional patents of somewhat less relevance, the relevant teachings and contents which are nevertheless incorporated herein by reference, include: U.S. Pat. No. 3,333,586 by Bellis et al, entitled "Eye-care devices"; and U.S. Pat. No. 7,069,084 by Yee, entitled "Method and apparatus for preventing and treating eyelid problems".

In addition to the foregoing patents, Webster's New Universal Unabridged Dictionary, Second Edition copyright 1983, is incorporated herein by reference in entirety for the definitions of words and terms used herein.

As may be apparent, in spite of the enormous advancements and substantial research and development that has been conducted, there still remains a need for an improved meibomian gland thermal treatment apparatus.

SUMMARY OF THE INVENTION

In a first manifestation, the invention is a meibomian gland thermal treatment apparatus. A battery-containing housing terminates at a thermal applicator tip. The thermal applicator tip has a face configured to apply thermal energy to a single eyelid meibomian gland region while an adjacent eyelid remains open. A power switch selectively couples electrical energy from the battery to the thermal applicator tip.

In a second manifestation, the invention is a meibomian gland thermal treatment apparatus. The apparatus has a housing having a telescopically sliding applicator head. At least one compression spring biases the telescopically sliding applicator head toward a fully extended position and is configured to mimic the force an eyelid applies during blinking to the meibomian gland. A thermal applicator tip terminates the housing and is supported by the telescopically sliding applicator head. The thermal applicator tip has a face configured to apply thermal energy to a single eyelid meibomian gland region while an adjacent eyelid remains open. The thermal applicator tip face is generally rectangular, extending in a longest direction along a first axis and in a shorter rectangular direction extends along a second axis. The thermal applicator tip face further has a concave curvature about an axis parallel to the second axis. A battery compartment within the housing contains a battery. An electrical compartment within the housing contains electrical components. There is an angular displacement in the housing between battery compartment and electrical compartment. A power switch selectively couples electrical energy from battery to thermal applicator tip. A treatment timer is coupled to the power switch and is configured to initiate a treatment timing cycle responsive to the power switch coupling electrical energy from the battery to the thermal applicator tip, and is configured to determine when a time duration of the treatment timing cycle has elapsed, and is configured to cause the power switch to uncouple electrical energy from battery to thermal applicator tip responsive to the treatment timing cycle elapse. An alerting device is configured to provide an alert indicative of the treatment timing cycle elapse.

In a third manifestation, the invention is a method of thermally treating meibomian gland dysfunction. According to the method, a thermal treatment apparatus is pressed against a meibomian gland region of a single closed one of a pair of eyelids. A second one of the pair of eyelids is opened subsequent to the pressing step sufficiently to use an eye encompassed by the pair of eyelids to perform tasks in addition to thermal treatment. A therapeutic temperature is maintained in the thermal treatment apparatus subsequent to the pressing step for a therapeutic time duration. The thermal treatment apparatus is inverted subsequent to the maintaining step. The thermal treatment apparatus is urged against a meibomian gland region of the second one of the pair of eyelids subsequent to the inverting step. A therapeutic temperature is held in the thermal treatment apparatus subsequent to the urging step for the therapeutic time duration.

Additional manifestations of the method of thermally treating meibomian gland dysfunction include such steps as: maintaining therapeutic temperature and therapeutic time duration to liquefy oil within the meibomian gland region of the single closed one of a pair of eyelids; biasing the thermal treatment apparatus against the meibomian gland region of the single closed one of a pair of eyelids at a substantially constant force an eyelid applies during blinking to the meibomian gland region of the single closed one of a pair of eyelids; and applying power to the thermal treatment apparatus responsive to the pressing step, disconnecting power to the thermal treatment apparatus responsive to an expiration of the therapeutic time duration, and providing a sensory alert responsive to the expiration of the therapeutic time duration.

OBJECTS OF THE INVENTION

Exemplary embodiments of the present invention solve inadequacies of the prior art by providing a meibomian gland thermal treatment apparatus that is comprised of a housing that is designed to be comfortably hand held during operation. Within the housing is a battery and necessary electrical and electronic components. A gentle bend between the battery compartment and electrical compartment improves ergonomics. A generally rectangular and concave thermal applicator tip terminates the housing, and is applied in direct thermal contact to a single eyelid. When held in a first position with the electrical compartment generally parallel to the ground and battery compartment sloping down toward the ground, a person may still keep their upper eye lid open, and still see out over the top of the housing. By inverting the meibomian gland thermal treatment apparatus and applying the thermal applicator tip on the upper lid, the electrical compartment is again generally parallel to the ground and the battery compartment slopes upward, allowing a person to keep their lower eye lid open, and again still see out around the housing. Consequently, a patient may perform the treatment with their eyes open or closed, while watching television, talking on the telephone, and performing other tasks. Owing to the simple geometry, a patient may also easily carry a preferred embodiment meibomian gland thermal treatment apparatus in a purse, hand bag, or pocket. Various embodiments also illustrate automatic on and off operation and a telescoping applicator having long-travel application force regulation.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to provide an improved, low cost, and portable meibomian gland thermal treatment apparatus well suited for home use to ensure good patient compliance. A second object of the invention is to provide an automated treatment cycle at precise temperature and pressure, so that the patient must only manipulate the apparatus into selected contact position relative to an eyelid, hold the apparatus, and then remove when appropriately signaled. Another object of the present invention is to ensure even contact and heating across the meibomian region of the eyelid. An additional object of the invention is the provision of an applicator head that is biased through a limited range of motion at the right force for application. A further object of the invention is to permit a patient to use the device for treatment while keeping both eyes open. Yet another object of the present invention is to enable a person to transport the apparatus discretely, such as in a purse, hand bag, or pocket.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

Figure 1:
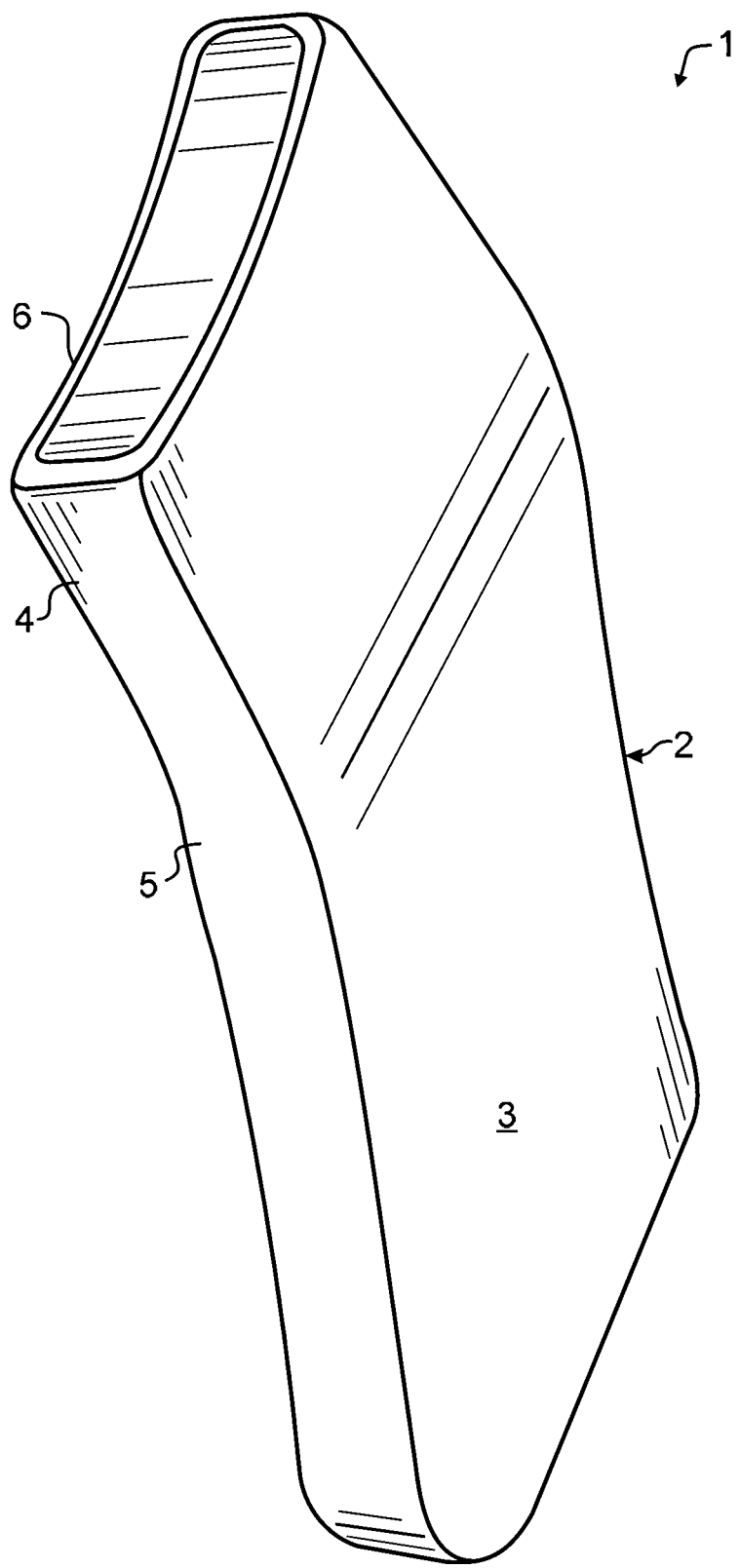
FIGS. 1 and 2 illustrate a preferred embodiment meibomian gland thermal treatment apparatus designed in accord with the teachings of the present invention from top projected and bottom projected views, respectively.
Figure 2:
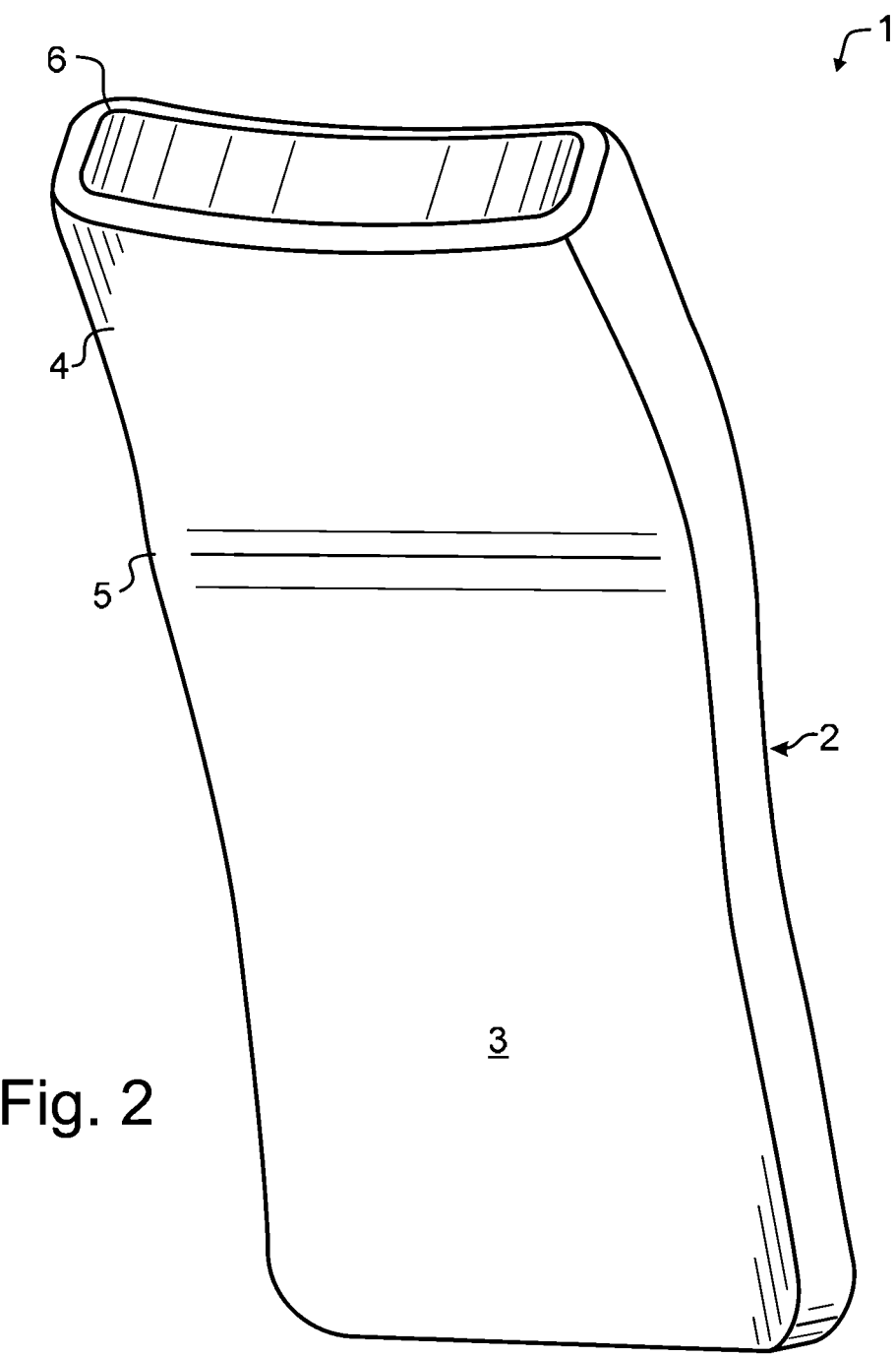
Figure 3:
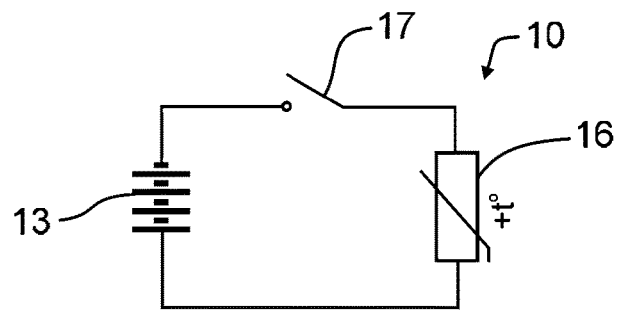
FIG. 3 illustrates the preferred embodiment meibomian gland thermal treatment apparatus of FIG. 1 from electrical schematic view.

Manifested in the preferred embodiment of the invention illustrated in FIGS. 1-3, the present invention provides a meibomian gland thermal treatment apparatus 1 that is comprised of a housing 2 that is designed to be comfortably hand held during operation. Housing 2 may be fabricated from any suitable material, but may preferably have a soft touch feel, such as might for exemplary purposes be provided by a low-durometer rubber or elastomeric exterior. Preferably, this exterior finish or coating will also preferably be readily cleaned and sterilized if so desired. Again for exemplary and non-limiting purposes, one suitable material is a silicone rubber.

A battery compartment 3 within housing 2 is preferably configured to contain a sufficiently large battery 13 to provide adequate energy through several warming treatments. An electrical compartment 4 within housing 2 is preferably configured to contain all necessary electrical and electronic components within electrical circuit 10. A gentle bend 5 is provided between battery compartment 3 and electrical compartment 4, which improves the ergonomics of preferred embodiment meibomian gland thermal treatment apparatus 1.

A thermal applicator tip 6 is provided that is configured to be in direct thermal contact with a single eyelid. Thermal applicator tip 6 is generally rectangular, extending in the longest direction along a first axis primarily across the width and from edge to edge of housing 2. The shorter rectangular dimension of thermal applicator 6 follows a second axis that extends primarily across the thickness of housing 2. In addition, thermal applicator tip 6 is preferably provided with a slight curvature about an axis parallel to the second axis that defines a slightly concave surface. This generally rectangular geometry, slightly curved out of plane to form a concave contact area, allows preferred embodiment meibomian gland thermal treatment apparatus 1 to be held easily and comfortably with thermal applicator tip 6 in thermal contact with the meibomian gland region of the lower lid. When held with the electrical compartment 4 generally parallel to the ground and battery compartment 3 sloping down toward the ground, a person may still keep their upper eye lid open, and still see out over the top of housing 2. This is in stark contrast to the prior art such as Smith et al that use either an oval or round applicator tip, which will necessarily block vision when applying heat to the meibomian gland region.

By inverting preferred embodiment meibomian gland thermal treatment apparatus 1 and applying thermal applicator tip 6 on the upper lid, electrical compartment 4 is again generally parallel to the ground and battery compartment 3 slopes upward, allowing a person to keep their lower eye lid open, and once again to still see out below the bottom of housing 2. Consequently, a patient may perform the treatment with their eyes open or closed. With the portable nature of preferred embodiment meibomian gland thermal treatment apparatus 1, a patient may perform the treatment while watching television, talking on the telephone, and other tasks. Owing to the simple geometry, a patient may also easily carry preferred embodiment meibomian gland thermal treatment apparatus 1 in a purse, hand bag, or pocket.

Preferred embodiment meibomian gland thermal treatment apparatus 1 applies heat to the margins of the eyelid in order to liquify oil within the meibomian glands. This allows specific warming to the oil glands instead of applying heat to the entire upper face and lids. When oil solidifies, the meibomian gland becomes blocked. When the gland remains blocked for a period of time, the gland atrophies and may ultimately be permanently destroyed. By keeping the meibomian glands healthy and with oil in a liquid state, preferred embodiment meibomian gland thermal treatment apparatus 1 helps to decrease damage to the oil glands and slow the progression of dry eye syndrome.

FIG. 3 illustrates preferred embodiment meibomian gland thermal treatment apparatus 1 schematically, and in simplest electrical form. Electrical circuit 10 includes a battery 13 contained within battery compartment 3. Battery 13 may for exemplary purposes, but not solely limiting the invention thereto, be either a disposable battery pack such as for exemplary and non-limiting purpose configured from alkaline cells, or may alternatively comprise a rechargeable battery pack such as a lithium-ion or nickel-metal-hydride battery. In the case of a rechargeable battery pack, a charger will necessarily be provided which might, for exemplary and non-limiting purposes, include any of the well-known USB chargers, a pogo pin charger providing a low voltage across the pogo pins using an AC adapter, an inductive charger such as a Qi charge circuit or one similar to those commonly found on electric toothbrushes, or other suitable charger.

An electrical switch 17 is provided so that electricity is selectively applied to Positive Temperature Coefficient (PTC) resistor 16. When not in use, electrical switch 17 will be in the open position (as illustrated), and so will not drain battery 13. Electrical switch 17 is not visible in FIGS. 1 and 2, but it will be understood that it may be located at any suitable position in housing 2.

When being used for treatment, electrical switch 17 is closed, and PTC resistor 16 will heat to a set temperature of approximately 109-110 degrees Fahrenheit, though the exact temperature will be selected by a circuit designer or ophthalmologist upon review of the present disclosure and consideration for a desired time and temperature regimen. PTC resistors of this type are well known, and can be fabricated from a variety of materials. Similar devices are produced in high quantity for greenhouse and household plant starting, and may for exemplary purposes be fabricated from a polymer film filled with conductive particles. Upon heating and expansion, the polymer film expands and fewer particles remain in contact with each other, increasing the electrical resistance of the film. As a result, films of this type tend to be very closely temperature regulating, and also tend to have a very consistent surface temperature across the film. This type of film may be directly in contact with a person's eyelid, but in the preferred embodiment a thin electrical dielectric layer is preferably provided to conduct heat to the eyelid without applying electricity thereto.

In one alternative embodiment, one or more discrete ceramic PTC devices may be used and thermally coupled to an aluminum or other thermally conductive bar. The aluminum bar may again be provided with a thin polymer layer such as a powder coating or paint, or an oxide or other ceramic coating or other protective finish. In a further embodiment, other thermally conductive materials besides aluminum may be used to transfer heat from the PTC device(s) to the patient's eyelid.

In another alternative embodiment, resistive wire and a protective heat transfer layer may be used as the heat source. However, resistive wire does not have intrinsic thermal regulation. Consequently, the use of resistive wire increases the complexity of the circuitry, and will also normally require the incorporation of at least one temperature sensor and a power regulation circuit that controls the power applied to the resistive wire based upon temperature of the resistive wire. Consequently, the use of a PTC heater is preferred.

As noted above, thermal applicator tip 6 is gently curved to correspond to a smaller than average or typical person's eyelid curvature, and thereby allow thermal applicator tip 6 to contact the entire eye lid or some portion less than the entire eyelid for most persons. In an alternative embodiment the eye-contacting portion of the thermal layer may be custom fabricated for a single patient to conform specifically to the patient's eyes. In yet another alternative embodiment, thermal applicator tip 6 may be provided in several different sizes and possibly different curvatures to fit the needs of larger numbers of patients.

In a further alternative embodiment, a conformal layer such as foam may be provided behind a film-type PTC resistor 16, or in another alternative embodiment, a void may be provided into which a resilient film-type PTC resistor 16 may flex and deform. In yet another alternative embodiment, the conformal layer may be in contact with the eyelid and comprise a thermally conductive material through which heat is effectively transferred. Such techniques allow thermal applicator tip 6 to conform to a wider range of eye shapes.

In a further alternative embodiment, a torque hinge or other known equivalent such as illustrated by Kossett in U.S. Pat. No. 8,875,348 and entitled "Friction hinge system", the teachings and content which are incorporated herein by reference, may be provided between battery compartment 3 and electrical compartment 4, to enable a person to set a comfortable angle there between. In addition, and where desired, an extension or other length adjustment may also optionally be provided. However, such extension will preferably not be too great in length as to present a hazard to a person using preferred embodiment meibomian gland thermal treatment apparatus 1.

Various embodiments of apparatus designed in accord with the present invention have been illustrated in the various figures. The embodiments are distinguished by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

Figure 4:
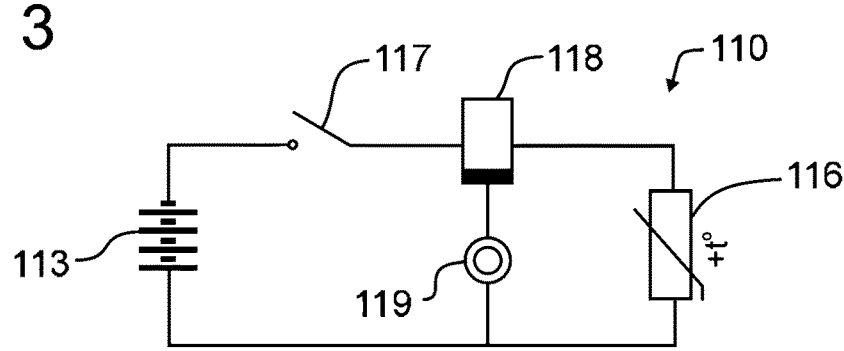
FIG. 4 illustrates a first alternative embodiment meibomian gland thermal treatment apparatus designed in accord with the teachings of the present invention from electrical schematic view.

FIG. 4 schematically illustrates a first alternative embodiment meibomian gland thermal treatment apparatus electrical circuit 110. A timer 118 is provided that will disconnect power to PTC resistor 116 after either a factory or user preset time period. A typical treatment time will be determined by a designer or ophthalmologist, but may for exemplary and non-limiting purposes run several minutes per eyelid. The timer frees the patient from having to monitor treatment time, and ensures that the device will shut down and not deplete the battery 113 even if the patient forgets to turn off electrical switch 117. In addition, an optional buzzer or other alerting device 119 may be provided to notify the patient through audible, tactile, visual, or other sensory input or combination of inputs that the treatment time has expired. In one embodiment, alerting device 119 may comprise in combination a small buzzer or tone generator and a small LED on the top surface of electrical compartment 4, which will be visible if the patient's eye is open. Consequently, either of the LED or tone will alert a person, so hearing impaired patients and patients who still prefer to close their eyes will be aware that the time has expired.

In an embodiment where an LED is provided for or as a part of alerting device 119, the LED may also be used as a status indicator. For exemplary and non-limiting purpose, the LED might be a tri-color LED, where a flashing red is indicative of a low-battery state, a yellow light is indicative of the apparatus being on but not to treatment temperature, and a green light indicative of the device being fully operational. In this embodiment, the colors and illumination state may, of course, be selected to suit the desires of a particular designer.

Figure 5:
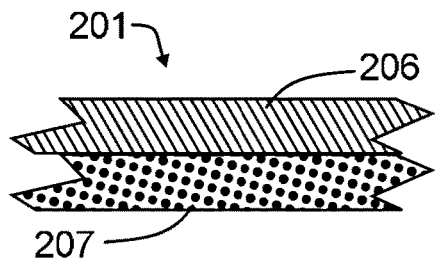
FIGS. 5 and 6 illustrate a second alternative embodiment meibomian gland thermal treatment apparatus designed in accord with the teachings of the present invention from a partial section view of the applicator and by electrical schematic view, respectively.

FIG. 5 illustrates a second alternative embodiment meibomian gland thermal treatment apparatus 201 from a sectional view taken through thermal applicator tip 206 and showing a conformal foam backing layer 207 as discussed herein above. However, in addition to being conformal to adapt to the shape of the eyelid, conformal foam backing layer 207 is also a conductive foam that is pressure sensitive. Consequently, circuitry may be provided to detect when pressure is applied to thermal applicator tip 206, and, responsive thereto, may energize PTC resistor 216. The force of a blink that pushes liquid oil from the meibomian glands is only a fraction of a Pound per Square Inch (PSI), and so the contact pressure between thermal applicator tip 206 and a patient's eyelid may also be quite low. Consequently, a very small force may be required to trigger conductivity in conformal foam backing layer 207.

Figure 6:
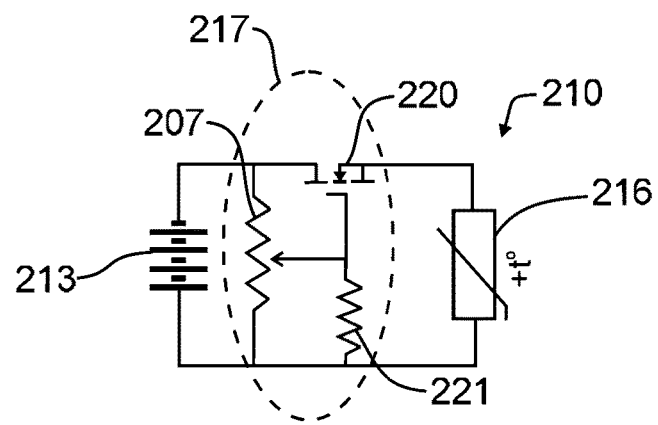

FIG. 6 illustrates second alternative embodiment meibomian gland thermal treatment apparatus electrical circuit 210. In this case, rather than or in addition to a power switch, a force that compresses conformal and electrically conductive foam backing layer 207, such as contact with an eye lid, will lead to greater conductivity there through. This may be detected, such as at a conductive electrode or layer adjacent to conformal foam backing layer 207 opposite or distal to thermal applicator tip 206. As illustrated in FIG. 6, this conductivity will form a voltage division between conformal foam backing layer 207 and resistor 221. The resulting voltage when great enough can trigger conductivity in transistor 220, thereby connecting electricity from battery 213 to PTC resistor 216, initiating heating in response thereto. As a result, the combination of conformal foam backing layer 207, transistor 220, and resistor 221 form an electronic switch 217.

In an alternative embodiment electronic switch 217, rather than detecting the impedance across conformal foam backing layer 207, electrodes are placed directly on the surface of thermal applicator tip 206 that measure skin impedance. Since skin impedance has a reasonable range, appropriate electronics may optionally be further provided to distinguish skin impedance from a direct metal contact, for example.

Figure 7:
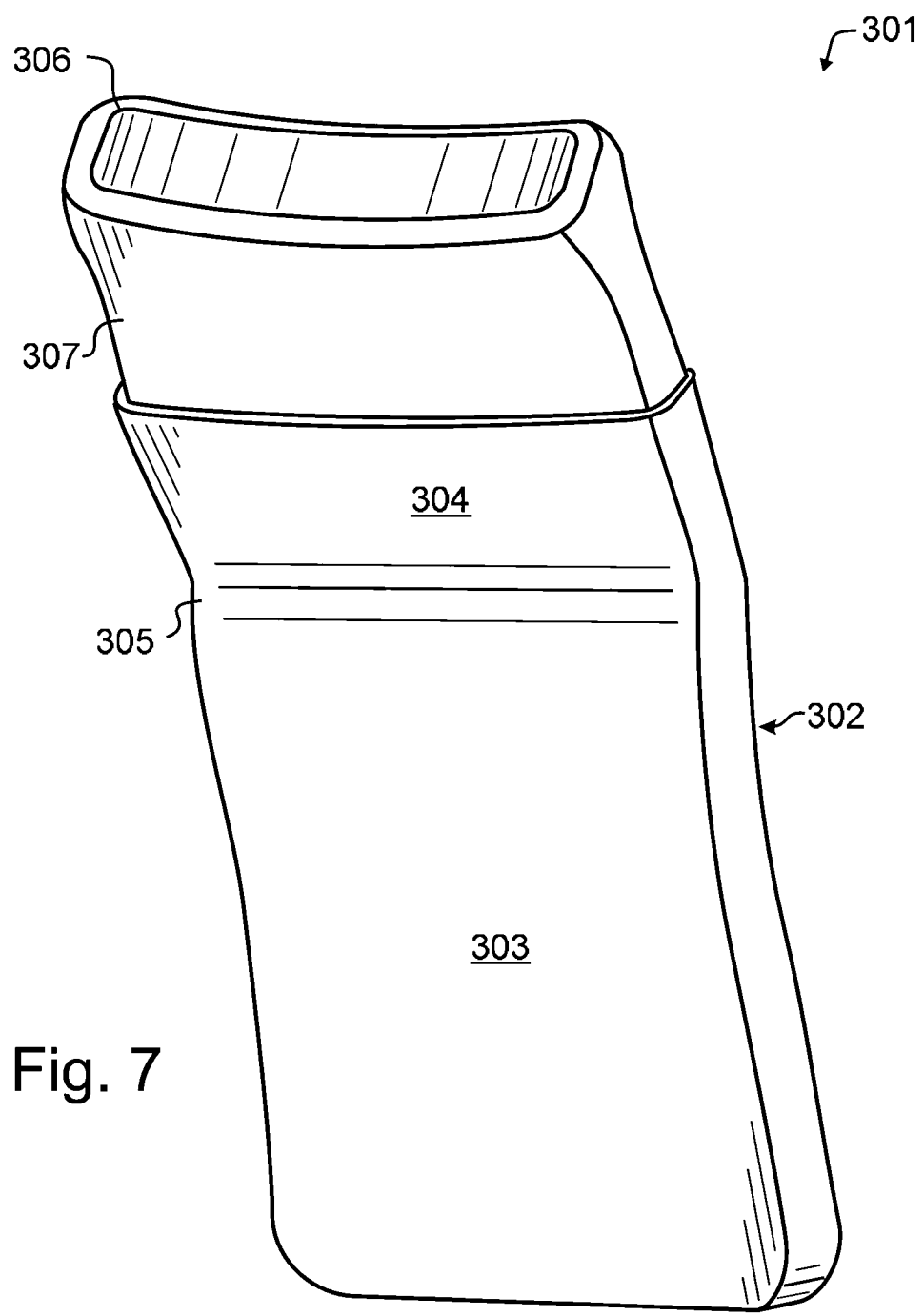
FIGS. 7 and 8 illustrate a third alternative embodiment meibomian gland thermal treatment apparatus designed in accord with the teachings of the present invention from a bottom projected view of the applicator in FIG. 7 and by electrical schematic and mechanical section view in FIG. 8.
Figure 8:
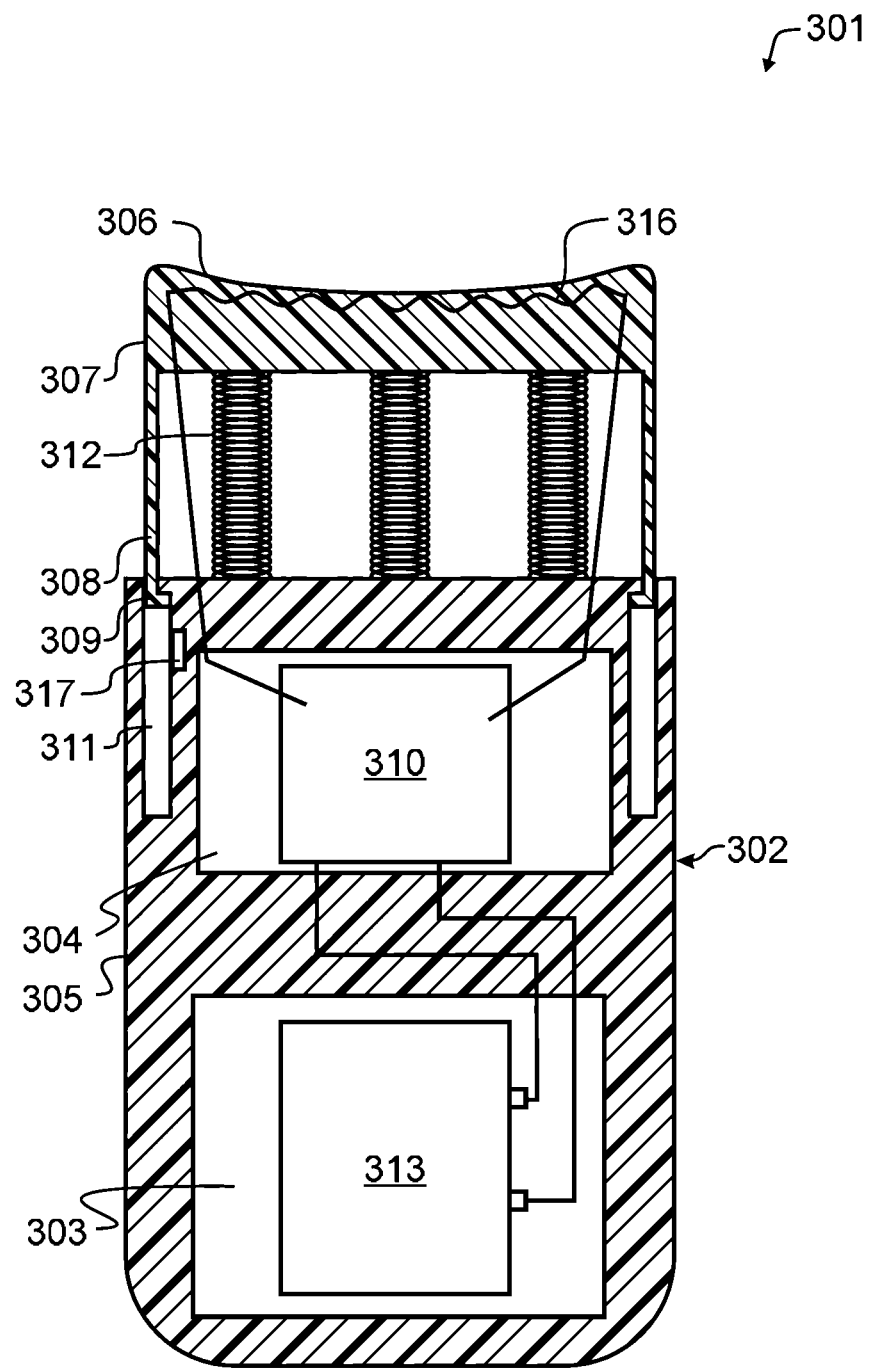

FIGS. 7 and 8 illustrate a third alternative embodiment meibomian gland thermal treatment apparatus 301. As visible in FIG. 7, a sliding applicator head 307 is designed to telescopically extend from electrical compartment 304. This is visible in the sectional view of FIG. 8. Sliding applicator head 307 may for exemplary and non-limiting purpose be provided with a depending skirt 308 that terminates at a small rim 309. Skirt 308 and rim 309 are configured to slide within a channel 311 formed within housing 302 in the vicinity of electrical compartment 304. One or more gentle compression springs 312 or known equivalents thereto are provided to very gently bias applicator head 307 away from battery compartment 303. Travel away therefrom is limited by rim 309 engaging with a matching rim within channel 311. Most preferably, compression springs 312 are selected to mimic the force of an eyelid during blinking, which is approximately 0.3 pounds per square inch (PSI). By fabricating them as longer travel springs, the force will not vary significantly during travel of skirt 308 within channel 311, thereby accommodating the slight movements that a person may make while holding thermal applicator tip 306 in contact with their eyelid. While a skirt 308, rim 309, and channel 311 are preferred, it will be understood that any other suitable linear or even arcuate track or slide known in the art may be provided in an alternative embodiment.

Either a prior art electro-mechanical switch such as electrical switch 17 or an impedance detector of any suitable type such as described herein above with regard to FIG. 6 may be used to activate third alternative embodiment meibomian gland thermal treatment apparatus 301. However, the movement of sliding applicator head 307 relative to channel 311 may instead be used to create several alternative embodiments for electrical switch 317.

Switch 317 in a first alternative embodiment comprises a rocker switch. In this embodiment, as rim 309 slides down over rocker switch 317, it will progressively travel across the rocker actuator, causing the switch to rock or flip to the on position. Then, when pressure is released from applicator head 307, springs 312 will return head 307 to the fully extended position. As this occurs, rim 309 will slide over and cause switch 317 to rock back to the off position. In a second alternative embodiment, a micro-switch may be provided that is pressed into an on position by rim 309 driving toward battery compartment 303. In a third alternative embodiment, a proximity detector is used to detect the present of skirt 308 or rim 309 within the adjacent portion of channel 311. The proximity detector may take many forms, and such devices as magnets and Hall magnetic field detectors may be used to detect proximity. In a fourth alternative embodiment, an optical detector may be used either by being blocked by skirt 308, or by a light beam reflected by skirt 308.

In any of these alternative embodiments of switch 317, the movement of sliding applicator head 307 activates switch 317 to initiate a treatment cycle. As may be apparent, the techniques described herein and the known equivalents thereto comprise a myriad of techniques known in the electro-mechanical arts that may be used to detect the movement of sliding applicator head 307 and activate switch 317, to initiate a treatment cycle.

Since sliding applicator head 307 is moveable, the conductors that are illustrated in FIG. 8 may be implemented through a variety of techniques, including for exemplary and non-limiting purposes: formation on a flex circuit; embedded into the housing; discrete conductors formed on housing halves; discrete conductors passing between housing halves; and other known equivalents.

From the foregoing figures and description, there are a number of unique features found in the present invention that may be incorporated into various embodiments designed in accord therewith. These features include: treatment for one eye lid at a time, so that the eye can remain open and functional during treatment; evenly warming the specific area of the meibomian glands; the provision of a self-contained electronic and portable apparatus that maintains a set temperature for a prescribed time period and doesn't require a secondary heat source; a treatment apparatus that curves to the contour of the eye lid, making it very comfortable; the provision of a sliding applicator head biased at the right force for application; and the incorporation of an automatic power switch. As a result, many embodiments designed in accord with the teachings of the present invention will be far easier for patients to use, and more patients will come into compliance with prescribed treatment, since they can conduct the treatment while focusing their eyes and primary attention to a computer, television, or while performing a variety of other tasks.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

We claim:

1. A meibomian gland thermal treatment apparatus, comprising:
   a housing;
   a thermal applicator tip terminating said housing and having a face configured to apply thermal energy to a single eyelid meibomian gland region while an adjacent eyelid remains open;
   a battery contained within said housing; and
   a power switch selectively coupling electrical energy from said battery to said thermal applicator tip;
   wherein said housing further comprises a telescopically sliding applicator head supporting said thermal applicator tip;
   further comprising a force biasing said telescopically sliding applicator head toward a fully extended position, said force configured to mimic the force an eyelid applies during blinking to the meibomian gland.

2. The meibomian gland thermal treatment apparatus of claim 1, wherein said thermal applicator tip face is generally rectangular, extending in a longest direction along a first axis and in a shorter rectangular direction extends along a second axis, said thermal applicator tip face further having a concave curvature about an axis parallel to said second axis.

3. The meibomian gland thermal treatment apparatus of claim 1, wherein said thermal applicator tip further comprises:
   a film-type PTC resistor; and
   a conformal foam layer.

4. The meibomian gland thermal treatment apparatus of claim 3, wherein said power switch further comprises an electronic switch.

5. The meibomian gland thermal treatment apparatus of claim 4, wherein said electronic switch further comprises:
   a pair of electrodes placed on an exterior surface of said thermal applicator tip; and
   an electronic circuit configured to selectively couple electrical energy from said battery to said thermal applicator tip when an impedance between said pair of electrodes is within a range that corresponds to skin impedance.

6. The meibomian gland thermal treatment apparatus of claim 4, wherein said conformal foam layer further comprises an electrically conductive foam, and wherein said electronic switch further comprises an electronic circuit configured to selectively couple electrical energy from said battery to said thermal applicator tip when an impedance through said conformal foam is within a range that corresponds to the force an eyelid applies during blinking to the meibomian gland.

7. The meibomian gland thermal treatment apparatus of claim 1, wherein said telescopically sliding applicator head further comprises:
   a skirt distal to said thermal applicator tip; and
   a small rim terminating said skirt distally to said thermal applicator tip.

8. The meibomian gland thermal treatment apparatus of claim 7, wherein said housing further comprises a channel adjacent to said skirt, said channel configured to slidably receive said skirt and said rim telescopically therein.

9. The meibomian gland thermal treatment apparatus of claim 8, wherein said power switch further comprises a skirt proximity detector.

10. The meibomian gland thermal treatment apparatus of claim 1, wherein said housing further comprises:
- a battery compartment configured to contain a battery;
- an electrical compartment configured to contain electrical and electronic components; and
- an angular displacement between said battery compartment and said electrical compartment.

11. The meibomian gland thermal treatment apparatus of claim 1, further comprising:
- a treatment timer coupled to said power switch and configured to initiate a treatment timing cycle responsive to said power switch coupling electrical energy from said battery to said thermal applicator tip, configured to determine when a time duration of said treatment timing cycle has elapsed, and configured to cause said power switch to uncouple said electrical energy from said battery to said thermal applicator tip responsive to said treatment timing cycle elapse; and
- an alerting device configured to provide an alert indicative of said treatment timing cycle elapse.

12. A meibomian gland thermal treatment apparatus, comprising:
- a housing;
- a thermal applicator tip terminating said housing and having a face configured to apply thermal energy to a single eyelid meibomian gland region while an adjacent eyelid remains open;
- a battery contained within said housing; and
- a power switch selectively coupling electrical energy from said battery to said thermal applicator tip;
- wherein said housing further comprises a telescopically sliding applicator head supporting said thermal applicator tip, said telescopically sliding applicator head having a skirt distal to said thermal applicator tip and a small rim terminating said skirt distally to said thermal applicator tip;
- wherein said housing further comprises a channel adjacent to said skirt, said channel configured to slidably receive said skirt and said rim telescopically therein; and
- wherein said power switch further comprises a micro switch actuated by movement of said skirt and said rim within said channel.

13. A meibomian gland thermal treatment apparatus, comprising:
- a housing;
- a thermal applicator tip terminating said housing and having a face configured to apply thermal energy to a single eyelid meibomian gland region while an adjacent eyelid remains open;
- a battery contained within said housing; and
- a power switch selectively coupling electrical energy from said battery to said thermal applicator tip;
- wherein said housing further comprises a telescopically sliding applicator head supporting said thermal applicator tip, said telescopically sliding applicator head having a skirt distal to said thermal applicator tip and a small rim terminating said skirt distally to said thermal applicator tip;
- wherein said housing further comprises a channel adjacent to said skirt, said channel configured to slidably receive said skirt and said rim telescopically therein; and
- further comprising at least one compression spring biasing said telescopically sliding applicator head toward a fully extended position and configured to mimic the force an eyelid applies during blinking to the meibomian gland, thereby accommodating slight movements that a person may make while holding said thermal applicator tip in contact with an eyelid.

14. A meibomian gland thermal treatment apparatus, comprising:
- a housing having a telescopically sliding applicator head and at least one compression spring biasing said telescopically sliding applicator head toward a fully extended position and configured to mimic the force an eyelid applies during blinking to the meibomian gland;
- a thermal applicator tip terminating said housing and supported by said telescopically sliding applicator head, said thermal applicator tip having a face configured to apply thermal energy to a single eyelid meibomian gland region while an adjacent eyelid remains open, said thermal applicator tip face being generally rectangular, extending in a longest direction along a first axis and in a shorter rectangular direction extends along a second axis, said thermal applicator tip face further having a concave curvature about an axis parallel to said second axis;
- a battery compartment within said housing configured to contain a battery;
- a battery contained within said battery compartment;
- an electrical compartment within said housing containing electrical components;
- an angular displacement in said housing between said battery compartment and said electrical compartment;
- a power switch selectively coupling electrical energy from said battery to said thermal applicator tip;
- a treatment timer coupled to said power switch and configured to initiate a treatment timing cycle responsive to said power switch coupling electrical energy from said battery to said thermal applicator tip, configured to determine when a time duration of said treatment timing cycle has elapsed, and configured to cause said power switch to uncouple said electrical energy from said battery to said thermal applicator tip responsive to said treatment timing cycle elapse; and
- an alerting device configured to provide an alert indicative of said treatment timing cycle elapse.

* * * * *